United States Patent
Huttner et al.

(10) Patent No.: US 11,638,788 B1
(45) Date of Patent: May 2, 2023

(54) NEEDLE SAFETY GUARD FOR TATTOO NEEDLE DEVICE

(71) Applicants: Bionix, LLC, Toledo, OH (US); Mayo Foundation for Medical Education and Research, Rochester, MN (US)

(72) Inventors: James Huttner, Sylvania, OH (US); Mackenzie Eickhoff Vocke, Napoleon, OH (US); Broc T. Giffey, Rochester, MN (US)

(73) Assignees: Bionix, LLC, Toledo, OH (US); Mayo Foundation For Medical Education And Research, Rochester, MN (US)

( * ) Notice: Subject to any disclaimer, the term of this patent is extended or adjusted under 35 U.S.C. 154(b) by 105 days.

(21) Appl. No.: 17/488,875

(22) Filed: Sep. 29, 2021

Related U.S. Application Data

(60) Provisional application No. 63/086,220, filed on Oct. 1, 2020.

(51) Int. Cl.
*A61M 5/32* (2006.01)
*A61M 5/315* (2006.01)

(52) U.S. Cl.
CPC ...... *A61M 5/3202* (2013.01); *A61M 5/31501* (2013.01); *A61M 5/31583* (2013.01); *A61M 2210/04* (2013.01)

(58) Field of Classification Search
CPC ............ A61M 5/3202; A61M 5/31501; A61M 5/31583; A61M 37/0076; A61M 37/00; A61M 37/0084; A01K 11/005
See application file for complete search history.

(56) References Cited

U.S. PATENT DOCUMENTS

| | | | | |
|---|---|---|---|---|
| 5,084,017 | A * | 1/1992 | Maffetone | ........... A61M 5/5066 604/110 |
| 2019/0125484 | A1* | 5/2019 | Giffey | ............... A61M 37/0084 |
| 2019/0374721 | A1* | 12/2019 | Smith | ............... A61M 5/31535 |

OTHER PUBLICATIONS www.infinitetattoo.en.alibaba.com https://infinitetattoo.en.alibaba.com/product/1600076904101-818165364/1207RL-Infinite-Tattoo-Needle-Cartridge-Membrane-Tattoo-Cartridge-Needle; Fancy Plastic (Suzhous) Co. Ltd., prior to Oct. 1, 2020.

BD Medication Preparation and Administration with BD SafetyGlide Needle; Important Usage Guidelines; Beckton, Dickinson and Company, prior to Oct. 1, 2020.

BD Medication Preparation and Administration with BD Eclipse Needle; Important Usage Guidelines; Beckton, Dickinson and Company, prior to Oct. 1, 2020.

* cited by examiner

*Primary Examiner* — Dung T Ulsh
(74) *Attorney, Agent, or Firm* — Marshall & Melhorn, LLC

(57) ABSTRACT

A needle guard for a manual tattooing device includes a device body and a spring-loaded plunger having a tattoo needle at one end. The plunger is mounted for translational movement within the device body by manual activation of the plunger. The device includes a locking mechanism such that, in a first position, the plunger can be translated to extend the tattoo needle outside of the device body. However, in a second position of the locking device, translational movement of the plunger is prevented, which in turn prevents the exposure of the tattoo needle outside the confines of the device body.

7 Claims, 10 Drawing Sheets

NEEDLE SAFETY GUARD FOR TATTOO
NEEDLE DEVICE

BACKGROUND OF THE INVENTION

A tattoo is a form of body modification where a design is made by inserting ink, dyes and pigments, either indelible or temporary, into the dermis layer of the skin to change the pigment. Tattooing is performed using needles, either single or "ganged" for a broader stroke, to introduce the dye into the skin. Traditionally, these needles were attached to motorized devices that facilitated the rapid needle-poke process. Such needles were often sterilized for re-use.

More recently tattoo needle (again single or ganged) have been incorporated into disposable cartridges that fit standardized motorized hand-pieces. This allows tattoo artists access to sterile, single-use equipment that protects the person receiving the tattoo from transmitted blood-borne infections. However, such disposable tattoo needle cartridges do not protect or prevent the tattoo artist from accidental needlestick injury and possible infection.

Needlestick injuries are common; 800,000 needlestick injuries occur each year in the United States, and 16,000 of these are likely to be contaminated by HIV, HBV and HCV. The Needlestick Safety and Prevention Act went into effect in April 2001 and was designed to reduce health care workers' exposure to bloodborne pathogens by requiring hospitals and clinics to consider and implement new technologies—i.e. safety needle guards (among others)—when they update their "exposure control plan".

Safety needle guards are devices or features that cover exposed "sharps" (e.g. needle points) to protect the user from accidental needlestick injury. Such safety needle guards may be "active" requiring an affirmative action by the user to engage the needle guard, or "passive" wherein the needle guard activates upon use of the needle. Currently, commercially available disposable tattoo cartridge needles are not equipped with safety needle guards of either type. Passive needle guards are not practical for tattoo needle cartridges as the repetitive skin-poke of the tattoo process would obviate its use.

SUMMARY OF THE INVENTION

The invention is a needle guard for a manual tattooing device includes a device body and a spring-loaded plunger having a tattoo needle at one end. The plunger is mounted for translational movement within the device body by manual activation of the plunger. The device includes a locking mechanism such that, in a first position, the plunger can be translated to extend the tattoo needle outside of the device body. However, in a second position of the locking device, translational movement of the plunger is prevented, which in turn prevents the exposure of the tattoo needle outside the confines of the device body.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE INVENTION

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

Safety needle guards may be "active," requiring an affirmative action by the user to engage the needle guard, or "passive" wherein the needle guard activates upon use of the needle. As stated earlier, the use of a passive needle guard is not practical for commercially available tattoo cartridge needles. The invention is an active safety needle guard for commercial tattoo cartridge needles.

Figure 1:
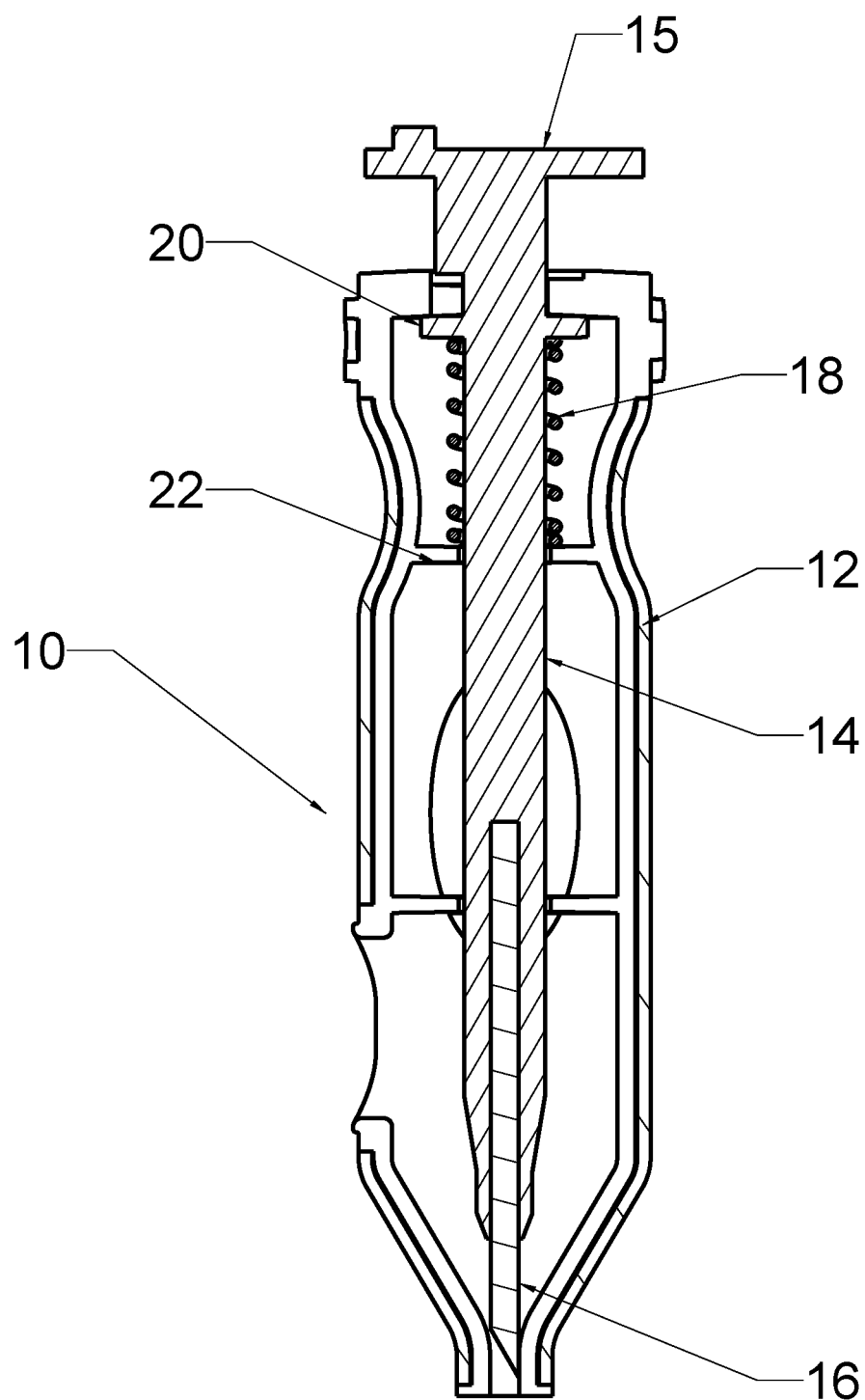
FIG. 1 is a cross-sectional view through an embodiment of a tattoo device with needle safety guard, showing the needle in a retracted position.

In the preferred embodiment illustrated in FIG. 1, the invention is an active safety needle guard for a manually operated tattooing device 10. In this embodiment, the manually operated tattooing device 10 preferably includes an elongate, hollow body 12 containing a plunger 14 with a needle 16 secured to or set into one end of the plunger 14. The opposite end of the plunger 14 is preferably provided with a radially enlarged top 15 to facilitate manipulation of the plunger 14 by a user of the device 10.

Figure 2:
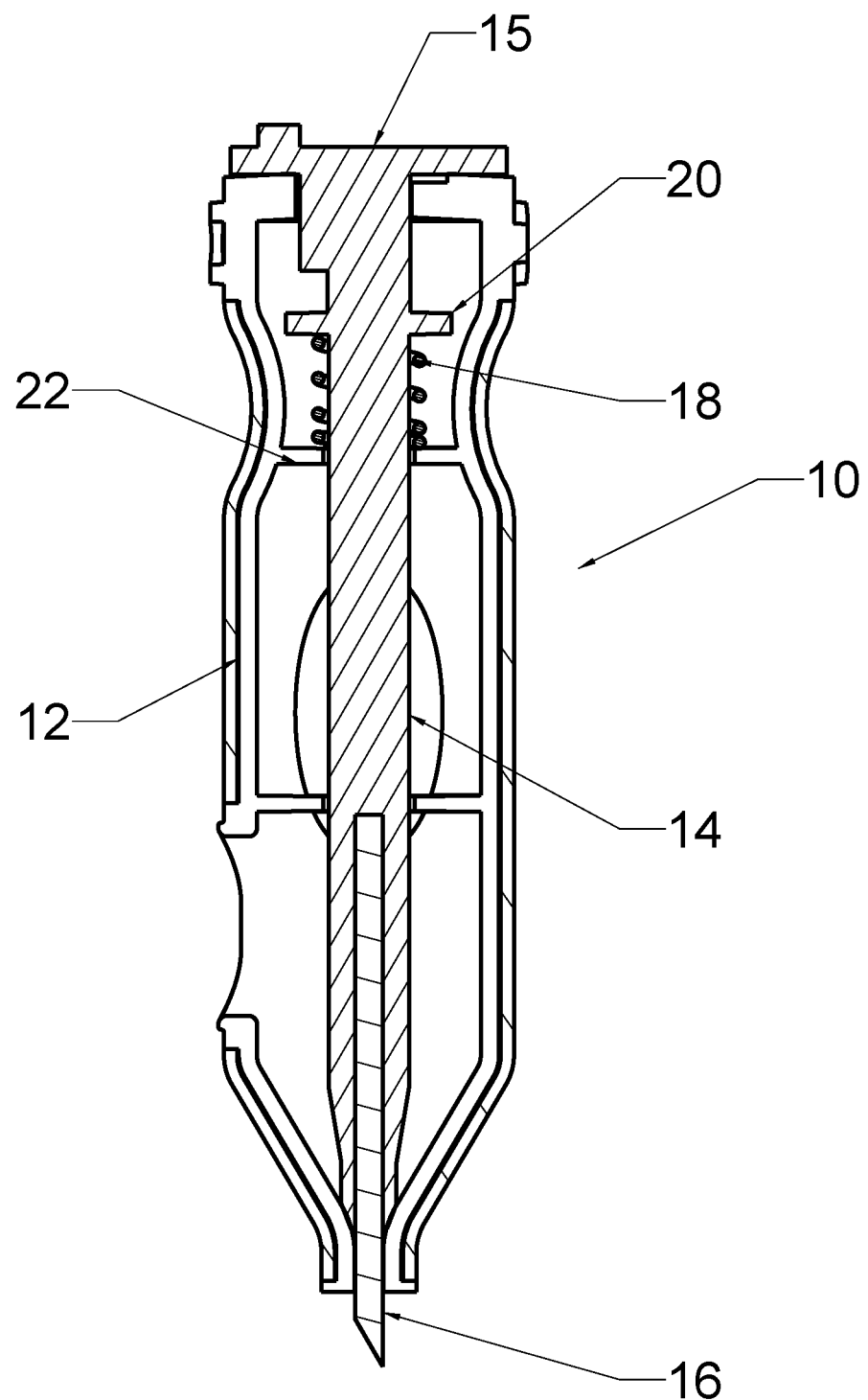
FIG. 2 is a cross-sectional view through the device of FIG. 1, showing the needle in an exposed position.

A spring 18 surrounds a portion of the plunger 14 and is seated with one end engaging an annular flange 20 formed on the plunger 14 and the opposite end engaging an annular flange 22 formed on the body 12. The spring 18 thereby urges the plunger 14 upwardly, as shown in FIG. 1, to maintain the needle 16 in a retracted position such that it is completely enclosed by and does not extend beyond the end of the body 12 of the tattooing device 10. The needle 16 is thus initially completely enclosed by the body 12 until the user is ready to administer a tattoo. Manually depressing the plunger 14 causes translational movement of the plunger 14 downwardly and exposes the needle 16 beyond the end of the body 12, as shown in FIG. 2, so that it may be used to produce a tattoo.

In accordance with an especially preferred embodiment of the invention, the plunger 14 and needle 16 can be rotationally disposed in three positions respective to the body 12 of the tattoo device 10. The positions include an active or open state in which the plunger 14 can be translated downwardly to extend the distal end of the needle 16 beyond the end of the body 12; a safe or temporary locked state in which the plunger 14 temporarily cannot be translated downwardly and the needle remains completely contained within the body 12; and a closed or permanently locked state in which the plunger 14 cannot be translated downwardly, the needle remains completely contained within the body 12, and the plunger 14 can no longer be positioned in the active state. Thus, these states refer to the ability of the plunger 14 to be manually depressed and are achieved by twisting the plunger 14 rotationally relative to the body 12. Signifiers on the outside of the body 12 and the plunger top 15 may be utilized to help a user identify the proper positioning of the device 10.

Figure 3:
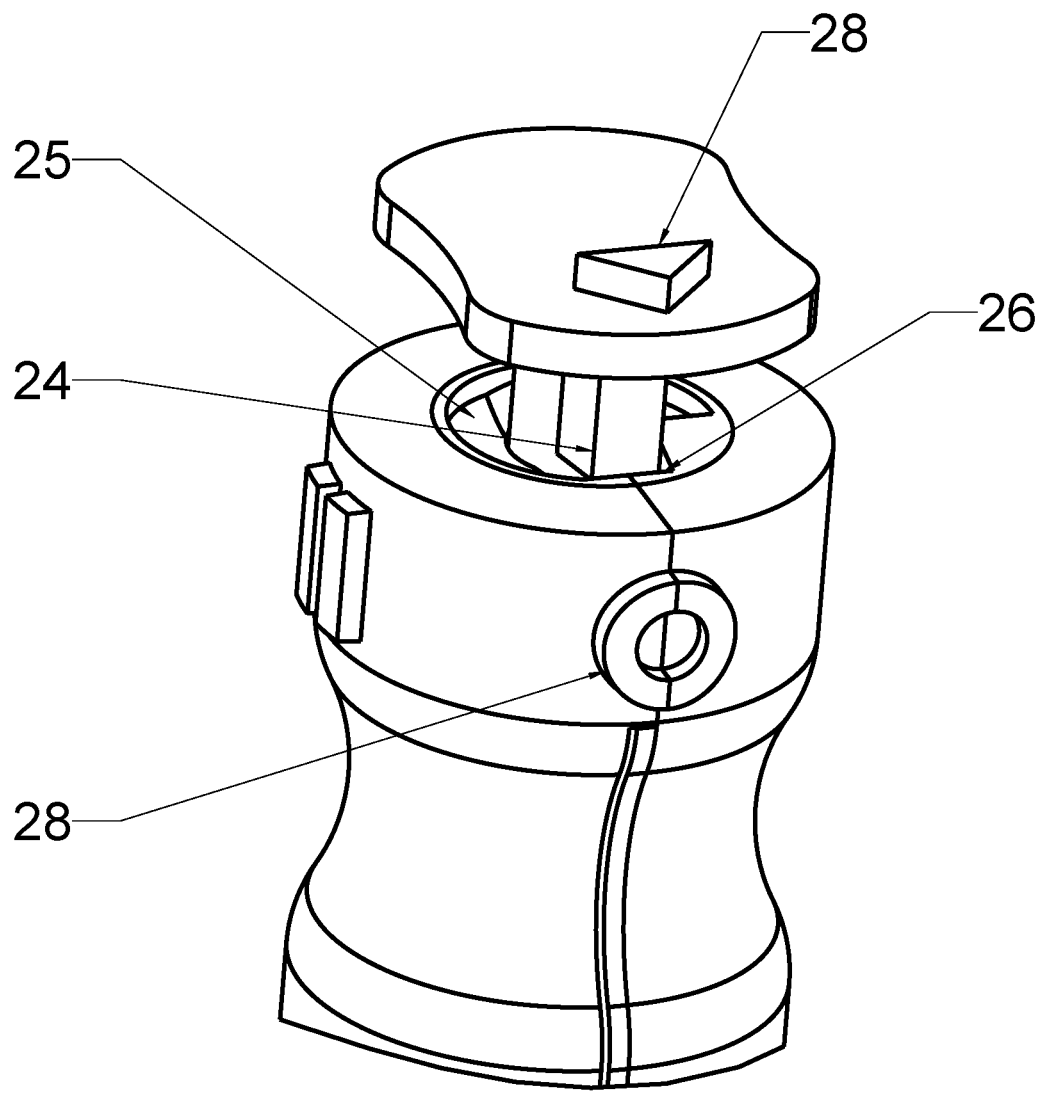
FIG. 3 is an enlarged perspective view of a portion of the device of FIG. 1, showing the plunger in the active position.
Figure 4:
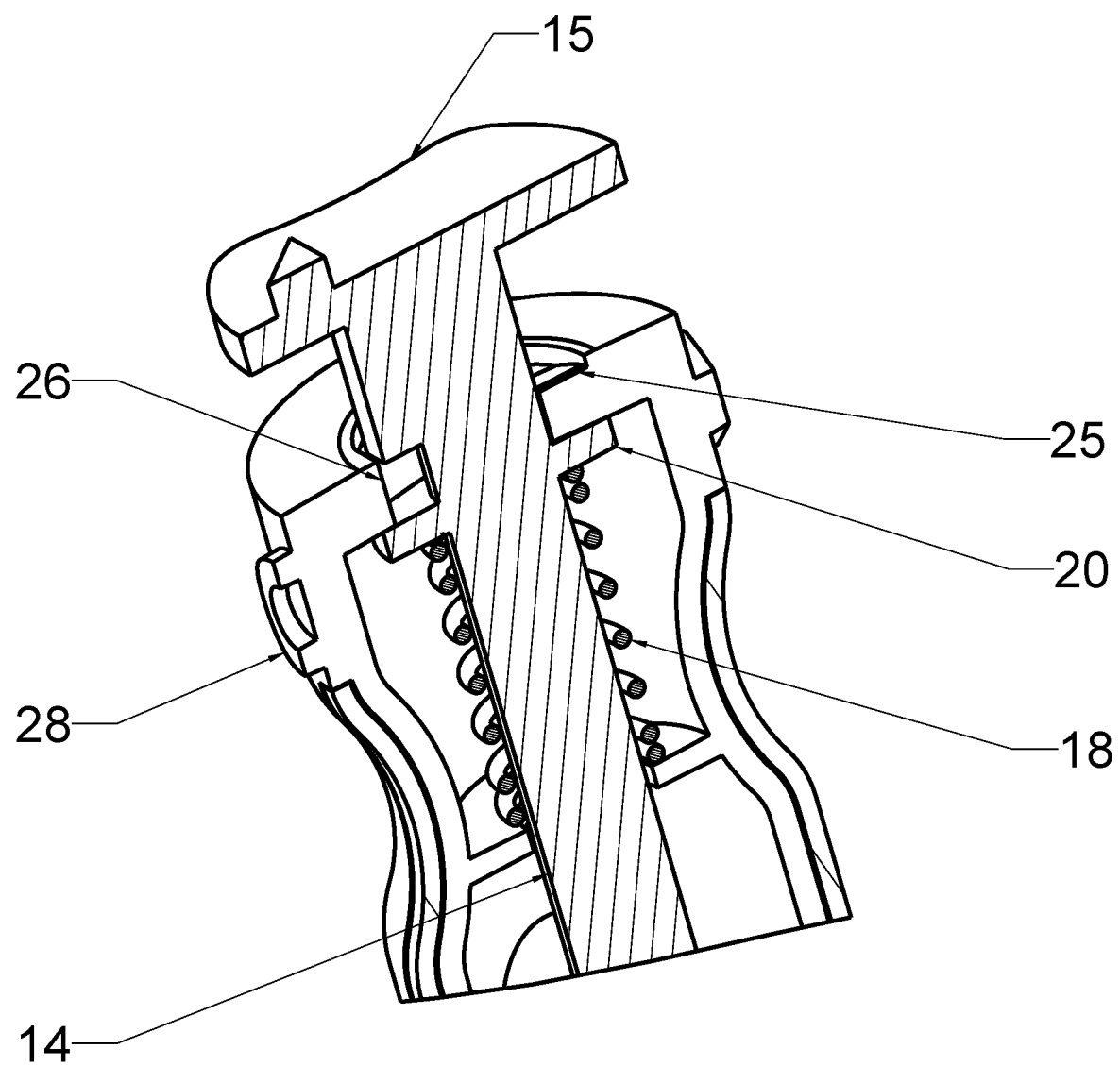
FIG. 4 is an enlarged, sectional perspective view of a portion of the device of FIG. 1, showing the plunger in the active position.
Figure 5:
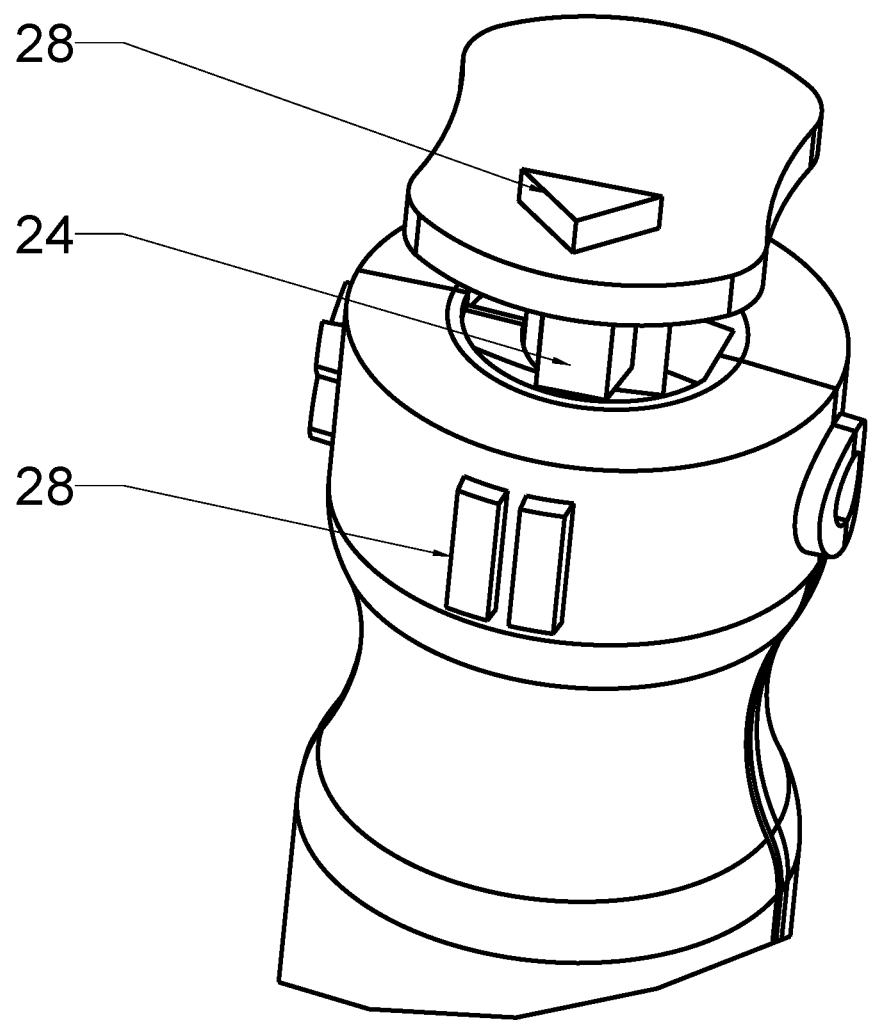
FIG. 5 is an enlarged perspective view of a portion of the device of FIG. 1, showing the plunger in the safe position.
Figure 6:
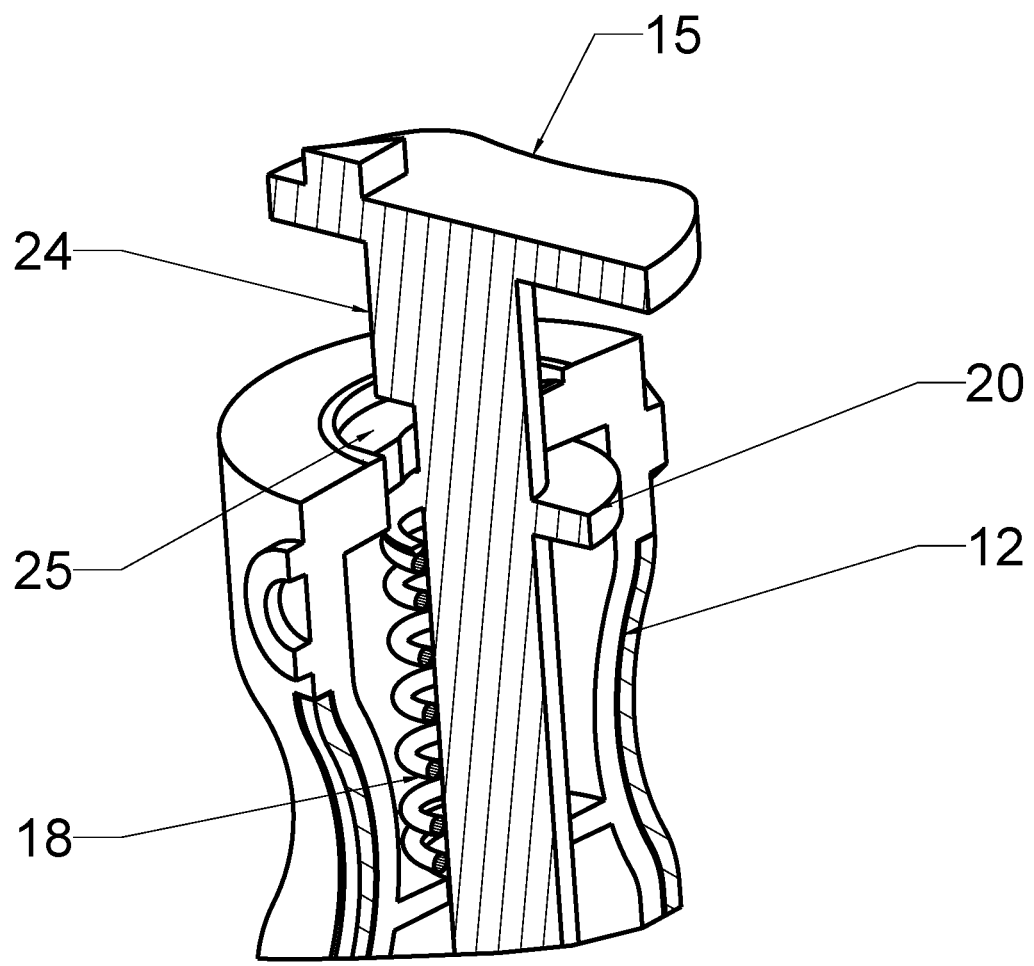
FIG. 6 is an enlarged, sectional perspective view of a portion of the device of FIG. 1, showing the plunger in the safe position.
Figure 7:
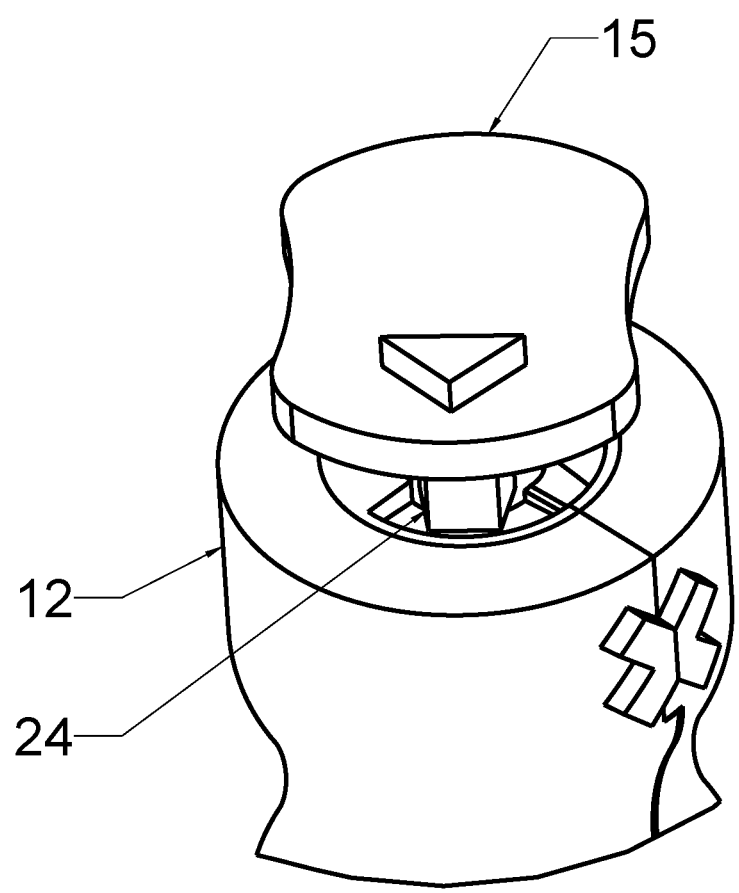
FIG. 7 is an enlarged perspective view of a portion of the device of FIG. 1, showing the plunger in the closed (locked) position.
Figure 8:
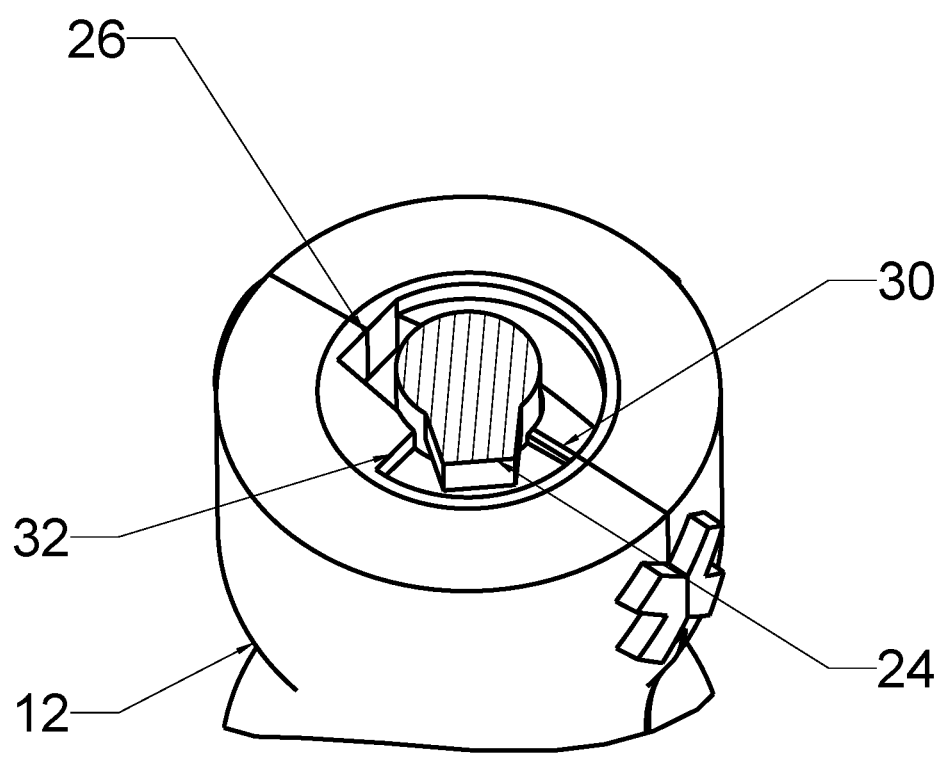
FIG. 8 is an enlarged perspective view of a portion of the device of FIG. 1, with the top of the plunger cut away and showing the plunger in the closed (locked) position.

Using the embodiment of FIGS. 1 and 2, FIGS. 3 and 4 illustrate the device in the active position, FIGS. 5 and 6 illustrate the device in the safe position, and FIGS. 7 and 8 illustrate the device in the locked position.

As shown, the active, safe, and closed positions are achieved utilizing the selective engagement of a radially outwardly extending protrusion 24 formed on the plunger 14 near its top 15 with one or more features formed on the upper surface 25 of the body 12.

Thus, in embodiments of the invention, the plunger 14 proximate its top 15 is cylindrical in shape but also includes the radially outwardly extending protrusion 24. The protrusion 24 may preferably have a generally trapezoidal shape with respect to a radially extending plane through the protrusion 24.

The upper surface 25 of the body 12 is provided with an aperture 26 having a shape that is complementary with the shape of the plunger 14 at the location along the length of the plunger 14 having the protrusion 24. When the plunger 14 is rotationally positioned relative to the body 12 such that the protrusion 24 aligns with the aperture 26 in the upper surface 25 of the body 12, the device 10 is in the active position.

FIG. 3 shows a close-up perspective view of the device 10 in the active position, with the plunger 14 shown rotated into the active or un-locked position. The alignment of symbols 28, such as the illustrated "X" on the top 15 of the plunger with the "O" on the outside of the body 12, may be utilized to provide a visual and/or tactile indication to a user that the device 10 is in the active state.

As shown in FIGS. 3 and 4, the protrusion 24 on the plunger 14 fits into the aperture 26 in the upper surface 25 of the body 12 in the manner of a key, allowing the plunger 14 to freely move axially with respect to the body 12 of the device 10, thereby further allowing the distal end or point of the needle 16 to be selectively exposed when the plunger 14 is manually depressed by a user.

FIGS. 5 and 6 show a close-up view, in perspective and cross-section, respectively, of the device 10 with the plunger 14 rotated (in a clockwise direction, when looking down on the plunger top 15 in these figures) relative to the body 12 so as to be in the safe or temporary lock position. When in the safe position, the protrusion 24 on the plunger 14 is not aligned with the complementary portion of the aperture 26 in the upper surface 25 of the body 12. The protrusion 24 preferably includes a flat surface facing and abutting a flat portion of the upper surface 25 of the body when in the safe position. This mechanical engagement prevents the plunger 14 from being depressed relative to the body 12, thereby preventing the needle 16 from being exposed beyond the end of the body. Placement of the device 10 in this position thus serves as a safety feature to prevent accidental exposure of the needle 16.

Again, in certain embodiments, the alignment of symbols 28 on the body 12 and the plunger 14 may aid in the determination that the device 10 is in the safe position. Further, the engagement of respective portions of the plunger 14 and the upper surface 25 of the body 12 may act as a physical signifier to provide a user with a tactile indication of the position of the plunger 14 relative the body 12, as long as such physical signifier does not prevent the plunger 14 from being rotated back to the open position, or from being further rotated into the "closed" or locked position as described below.

To administer a tattoo, the user presses down on the plunger 14 when the plunger 14 is in the active state, urging the top 15 of the plunger 14 toward the body 12 to expose the needle 16 beyond the end of the body 12 and administer a tattoo. When the user releases the plunger 14, the spring 18 urges the plunger upward, away from the body 12, and the needle 16 retracts back into the device body 12. The plunger 14 can then be rotated relative to the body 12 to place the device in the safe or temporary lock position. In this safe position, the plunger 14 engages a portion of the upper surface 25 of the body 12 to mechanically prevent depression of the plunger 14. Positioning of the device 10 in the safe position prevents unintended exposure of the needle 16 and protects the user when moving between tattooing sites.

FIGS. 7 and 8 show close-up views of the device 10 in the closed or locked position. In this position, the plunger 14 has been rotated further relative to the body 12 (again, in a clockwise direction, when looking down on the plunger top 15 in these figures). In the cut-away view of FIG. 8, the top 15 of the plunger 14 has been omitted to better show the features that cooperate to create the locked position in the illustrated embodiment. The upper surface 25 of the body 12 of the device 10 has a second flat area that also engages the protrusion 24 on the plunger 14, preventing the plunger 14 from being depressed. In a preferred embodiment, this second flat area of the upper surface 25 is also provided with first and second stops 30, 32 that extend from the upper surface 25 upwardly in a longitudinal direction toward the plunger top 15. The second stop 32 is circumferentially spaced apart from the first stop 30, such that there is sufficient space between the stops 30, 32 for the protrusion 24 to rest on the second flat area of the upper surface 25.

The first stop 30 is configured such that, upon rotation of the plunger 14 in a first direction relative to the body 12, the protrusion 24 is able to pass over the first stop 30 to come to rest on the flat area of the upper surface 25 between the stops 30, 32. However, when the user attempts to rotate the plunger 14 in the opposite direction relative to the body 12, the protrusion 24 abuts a surface of the first stop 10 so that it is unable to pass thereover. In certain embodiments, this may be accomplished by forming the first stop 30 with a side away from the second stop 32 that rises gradually in an incline from the upper surface 25 and the side nearest the stop 32 that rises relatively abruptly from and is preferably perpendicular to the second flat area of the upper surface 25.

Accordingly, once the device 10 has been placed in the closed or locked position, the engagement of the protrusion 24 between the stops 30, 32 prevents further rotation of the plunger 14 to either of the other positions, permanently locking the device in a state in which the plunger 14 cannot be depressed and the needle 16 cannot be extended outside of the confines of the body 12. Thus, once the user has administered all desired tattoos, the plunger can be placed in the permanently locked position for disposal of the device.

Figure 9:
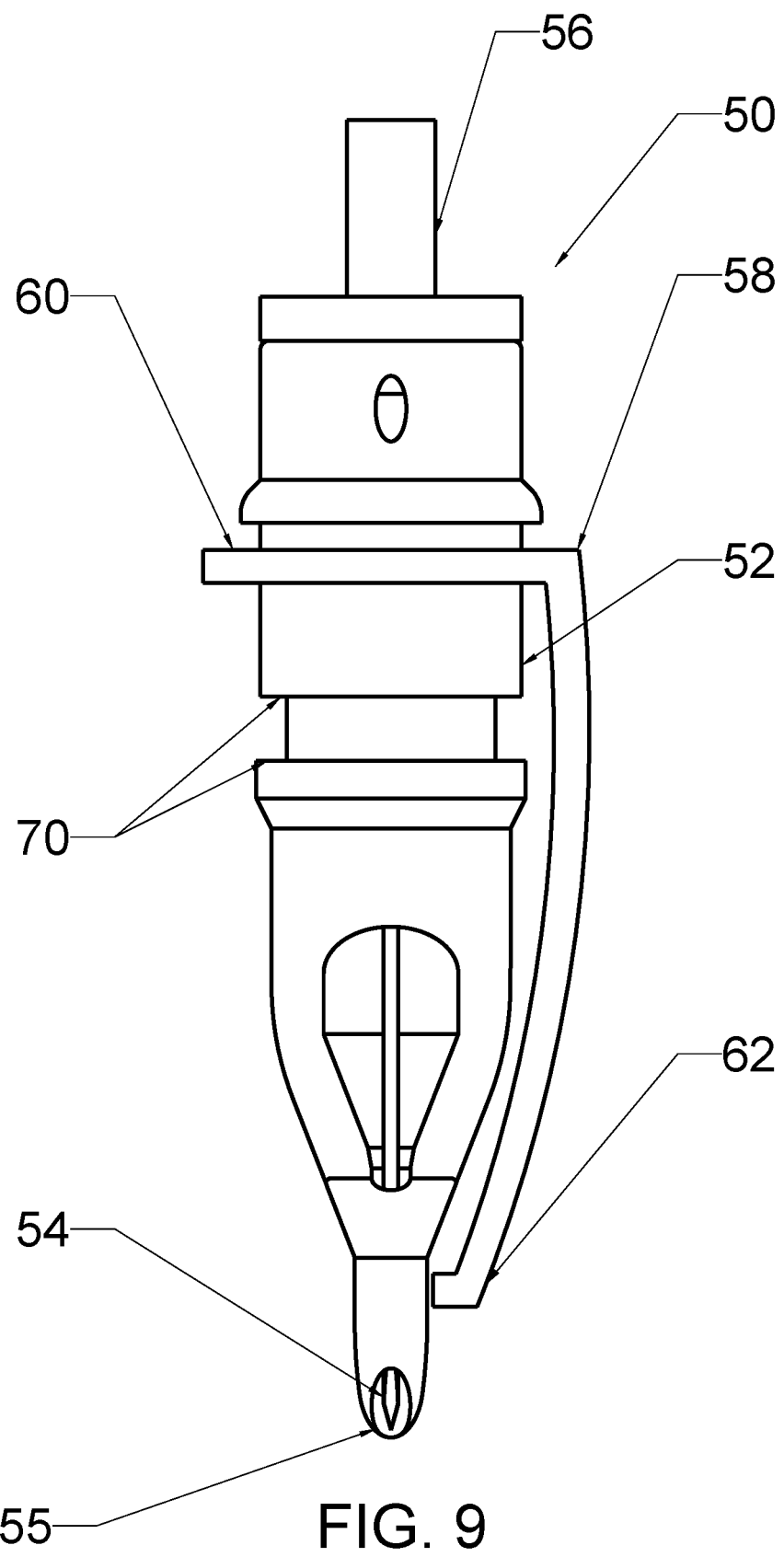
FIG. 9 is a plan view of an alternative embodiment of a device in accordance with the invention with the needle safety guard in an unengaged position.

In an alternate embodiment, an active safety needle guard is provided for commercial tattoo cartridge needles. FIG. 9 illustrates a tattoo cartridge 50 includes a housing 52 within which a tattoo needle 54 is mounted for selective translational movement between a retracted position in which the end of the needle 54 is completely contained within the housing 52 and an extended position (not shown) in which the end of the needle 54 extends through an opening 55 beyond the housing 52 and is exposed. A plunger 56 secured to the needle 54 may be manually depressed by a user to move the needle 54 to the extended position.

A needle guard 58 having a base portion 60 secured to the exterior of the housing 52 so as to be slidable in a longitudinal direction relative to the housing 52. The base portion 60 extends about and is in engagement with at least a portion of and preferably the entirety of a circumference of the housing 52. The needle guard 58 includes a needle cover portion 62 extending from the base portion 60, and having a distal end that is biased radially inwardly and is adapted to cover the opening 55 in the housing 52 through which the end of the needle 54 may be selectively extended.

When in the open or unengaged position illustrated in FIG. 9, the needle guard 58 sits with its base portion 60 on the housing 52 above a pair of slide stops 70 secured to the housing 52, the slide stops being longitudinally spaced apart one from the other. In this position, the distal end of the needle cover portion 62 of the needle guard 58 is biased into contact with an exterior surface of the housing 52.

Figure 10:
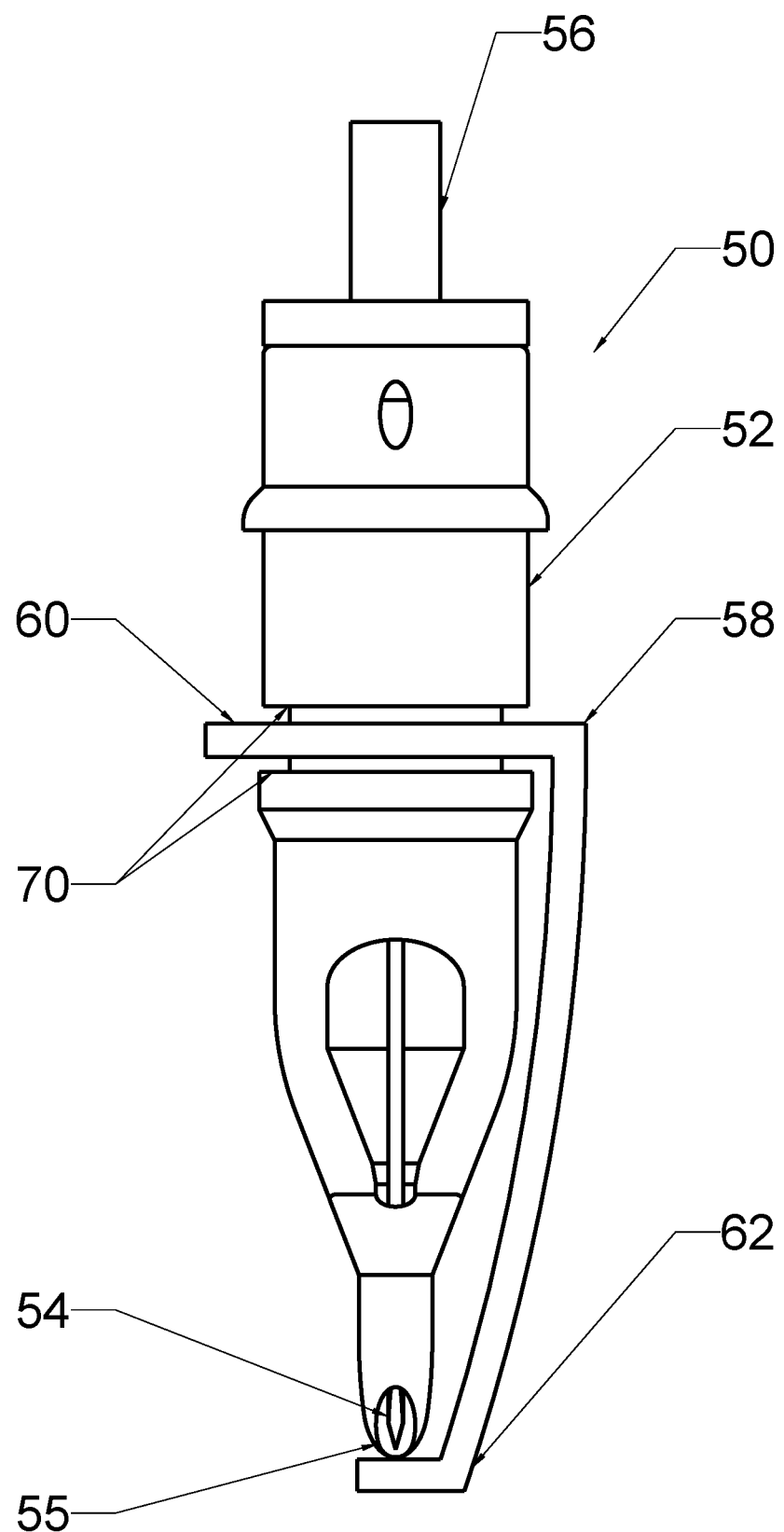
FIG. 10 is a plan view of the device of FIG. 9 with the needle safety guard in an engaged position.

The base portion 60 of the needle guard 58 is slideable along the housing 52 of the device, and so may be moved downwardly by a user to place the needle guard 58 in the locked or engaged position, as shown in FIG. 10. In this positon, the base portion 60 of the needle guard 58 is positioned between the two slide stops 70, and the needle cover portion 62 of the needle guard 58, being biased radially inwardly, moves into a position covering the opening 55 in the end of the housing 52, thereby preventing extension of the needle 54 therethrough.

In a preferred embodiment, the slide stops 70 are formed with the sides facing one another rising relatively abruptly from and preferably being perpendicular to exterior surface of the housing 52. As a result, once the base portion 60 of the needle guard 58 is slid into position between the two stops 70, it is prevented from sliding further in either direction, thereby permanently locking the needle cover portion 62 in the engaged or locked position.

The safety needle guard in accordance with various embodiments of the invention is simple to operate, has one or more sensory cues as to when it is un-engaged or engaged, preferably forms an integral part of the device and should form a barrier between the user's hands and the needle, and the protection it affords is preferably in place before and after disposal.

In accordance with the provisions of the patent statutes, the invention has been described in what is considered to represent its preferred embodiments. However, it should be noted that the invention could be practiced otherwise than as specifically illustrated and described without departing from its spirit or scope.

What is claimed is:

1. A needle guard for a manual tattooing device comprising:
   a manual tattoo device body; and
   a spring-loaded plunger having a tattoo needle at one end mounted for translational movement within the device body by manual activation of the plunger, the plunger including a protrusion;
   wherein in a first position the plunger can be translated to extend the tattoo needle outside of the device body, wherein upon rotation of the plunger to a second position relative to the device body, the protrusion on the plunger engages a surface of the device body to prevent translation of the plunger and thereby prevent the exposure of the tattoo needle outside the confines of the device body, and wherein the plunger can be rotated relative to the device body to a third position in which the protrusion on the plunger is positioned between a pair of mechanical stops such that the plunger cannot be rotated back to either the first position or the second position, and in which the protrusion on the plunger engages a surface of the device body to prevent translation of the plunger and thereby prevent the exposure of the tattoo needle outside the confines of the device body.

2. The needle guard of claim 1, wherein the plunger is capable of being rotated from the second position back to the first position.

3. The needle guard of claim 1, wherein the protrusion on the plunger fits into an aperture formed in an upper surface of the device body when the plunger is in the first position.

4. The needle guard of claim 1, wherein the plunger and the device body are each provided with a signifier, the respective signifiers aligning when the plunger is in the first position or the second position relative to the device body.

5. The needle guard of claim 1, wherein a first one of the pair of mechanical stops a side formed with a more gradual incline than that formed on an opposite side.

6. A needle guard for a tattoo cartridge needle comprising:
   an elongate housing defining a longitudinal axis;
   a tattoo needle mounted for translational movement within the housing between a first position in which the needle is completely contained within the housing and a second position in which the distal end of the needle extends through and beyond an opening in the housing;
   a slideable base portion circumferentially or partially circumferentially engaged around the housing;
   a needle cover extending from the slideable base portion and being biased radially inwardly towards the longitudinal axis of the housing, and
   a pair of spaced apart slide stops positioned on the housing, wherein when the slidable base portion is positioned between the slide stops, the slide stops prevent further sliding movement of the base portion in either direction and the needle cover moves into a position covering the opening in the housing.

7. The needle guard of claim 6, wherein the slideable member may be manually slid down the tattoo cartridge body to the locked position.

* * * * *